United States Patent
Belson et al.

(10) Patent No.: US 11,844,625 B2
(45) Date of Patent: Dec. 19, 2023

(54) INSTRUMENTED WOUND CLOSURE DEVICE

(71) Applicant: ZIPLINE MEDICAL, INC., Campbell, CA (US)

(72) Inventors: Amir Belson, Los Altos, CA (US); Edward C. Driscoll, Jr., Portola Valley, CA (US); Eric Storne, Menlo Park, CA (US); Alan Schaer, San Jose, CA (US)

(73) Assignee: Zipline Medical, Inc., Campbell, CA (US)

( * ) Notice: Subject to any disclaimer, the term of this patent is extended or adjusted under 35 U.S.C. 154(b) by 266 days.

(21) Appl. No.: 17/113,602

(22) Filed: Dec. 7, 2020

(65) Prior Publication Data

US 2021/0106276 A1 Apr. 15, 2021

Related U.S. Application Data

(60) Division of application No. 15/201,088, filed on Jul. 1, 2016, now Pat. No. 10,888,269, which is a
(Continued)

(51) Int. Cl.
*A61B 5/00* (2006.01)
*A61N 5/06* (2006.01)
(Continued)

(52) U.S. Cl.
CPC .......... *A61B 5/4848* (2013.01); *A61B 5/0015* (2013.01); *A61B 5/01* (2013.01);
(Continued)

(58) Field of Classification Search
CPC ................ A61B 17/085; A61B 5/1121; A61B 2017/00221; A61B 2017/00893; A61B 2090/064
See application file for complete search history.

(56) References Cited

U.S. PATENT DOCUMENTS 2,012,755 A 8/1935 Muth
2,371,978 A 3/1954 Perham
(Continued)

FOREIGN PATENT DOCUMENTS

CN 1126430 A 7/1996
CN 1442119 A 9/2003
(Continued)

OTHER PUBLICATIONS

Office action dated Nov. 19, 2012 for U.S Appl. No. 13/096,602.
(Continued)

*Primary Examiner* — Alexander J Orkin
(74) *Attorney, Agent, or Firm* — Bookoff McAndrews, PLLC

(57) ABSTRACT

A wound or incision closure apparatus comprises a first and second panel. Each of the panels comprises a bottom adhesive layer, a medial substrate layer, and an upper load distribution layer which connect the two panels. A sensory or therapeutic element is disposed adjacent, within, or between two or more of the layers. The sensory or therapeutic element can provide sensing and/or therapy for the incision and/or monitor the incision so that the therapy can be customized and updated.

18 Claims, 8 Drawing Sheets

Related U.S. Application Data continuation of application No. PCT/US2015/010188, filed on Jan. 5, 2015.

(60) Provisional application No. 61/964,477, filed on Jan. 5, 2014.

(51) Int. Cl.
| | | |
|---|---|---|
| A61B 5/145 | (2006.01) | |
| A61M 31/00 | (2006.01) | |
| A61N 7/00 | (2006.01) | |
| A61F 7/00 | (2006.01) | |
| A61B 17/08 | (2006.01) | |
| A61H 23/02 | (2006.01) | |
| A61H 23/00 | (2006.01) | |
| A61N 1/00 | (2006.01) | |
| A61B 5/01 | (2006.01) | |
| A61B 5/11 | (2006.01) | |
| A61B 17/00 | (2006.01) | |
| A61B 90/00 | (2016.01) | |

(52) U.S. Cl.
CPC ........... *A61B 5/1118* (2013.01); *A61B 5/1121* (2013.01); *A61B 5/14532* (2013.01); *A61B 5/14539* (2013.01); *A61B 5/14542* (2013.01); *A61B 5/6832* (2013.01); *A61B 5/746* (2013.01); *A61B 17/08* (2013.01); *A61B 17/085* (2013.01); *A61F 7/007* (2013.01); *A61H 23/00* (2013.01); *A61H 23/02* (2013.01); *A61H 23/0245* (2013.01); *A61M 31/002* (2013.01); *A61N 1/00* (2013.01); *A61N 5/0616* (2013.01); *A61N 5/0624* (2013.01); *A61N 7/00* (2013.01); *A61B 2017/00022* (2013.01); *A61B 2017/0073* (2013.01); *A61B 2017/00075* (2013.01); *A61B 2017/00084* (2013.01); *A61B 2017/00221* (2013.01); *A61B 2017/00407* (2013.01); *A61B 2017/00876* (2013.01); *A61B 2017/00893* (2013.01); *A61B 2017/086* (2013.01); *A61B 2090/064* (2016.02); *A61B 2562/0219* (2013.01); *A61B 2562/0223* (2013.01); *A61B 2562/0261* (2013.01); *A61B 2562/0266* (2013.01); *A61F 2007/0052* (2013.01); *A61F 2007/0056* (2013.01); *A61H 2201/0184* (2013.01); *A61H 2201/0207* (2013.01); *A61H 2201/0214* (2013.01); *A61H 2201/0242* (2013.01); *A61H 2201/10* (2013.01); *A61H 2201/105* (2013.01); *A61H 2201/165* (2013.01); *A61H 2201/5015* (2013.01); *A61H 2201/5058* (2013.01); *A61H 2201/5061* (2013.01); *A61H 2201/5064* (2013.01); *A61H 2201/5084* (2013.01); *A61H 2201/5092* (2013.01); *A61H 2201/5097* (2013.01); *A61H 2230/00* (2013.01); *A61H 2230/205* (2013.01); *A61H 2230/207* (2013.01); *A61H 2230/505* (2013.01)

(56) References Cited

U.S. PATENT DOCUMENTS

| | | |
|---|---|---|
| 2,747,248 A | 5/1956 | Mercer |
| 3,118,201 A | 1/1964 | Beghetto, Jr. |
| 3,487,836 A | 1/1970 | Niebel et al. |
| 3,516,409 A | 6/1970 | Howell |
| 3,698,395 A | 10/1972 | Hasson |
| 3,863,640 A | 2/1975 | Haverstock |
| 3,926,193 A | 12/1975 | Hasson |
| 3,933,158 A | 1/1976 | Haverstock |
| 3,971,384 A | 7/1976 | Hasson |
| 3,972,328 A | 8/1976 | Chen |
| 3,983,878 A | 10/1976 | Kawchitch |
| 4,038,989 A | 8/1977 | Romero-Sierra et al. |
| 4,114,624 A | 9/1978 | Haverstock |
| 4,210,148 A | 7/1980 | Stivala |
| 4,222,383 A | 9/1980 | Schossow |
| 4,224,945 A | 9/1980 | Cohen |
| 4,526,173 A | 7/1985 | Sheehan |
| 4,531,521 A | 7/1985 | Haverstock |
| 4,535,772 A | 8/1985 | Sheehan |
| 4,539,990 A | 9/1985 | Stivala |
| 4,576,163 A | 3/1986 | Bliss |
| 4,605,005 A | 8/1986 | Sheehan |
| 4,612,230 A | 9/1986 | Liland et al. |
| 4,676,245 A | 6/1987 | Fukuda |
| 4,702,251 A | 10/1987 | Sheehan |
| 4,780,168 A | 10/1988 | Beisang et al. |
| 4,871,367 A | 10/1989 | Christensen et al. |
| 4,881,546 A | 11/1989 | Kaessmann |
| 4,905,694 A | 3/1990 | Will |
| 4,950,282 A | 8/1990 | Beisang et al. |
| 4,966,605 A | 10/1990 | Thieler |
| 4,976,726 A | 12/1990 | Haverstock |
| 5,176,703 A | 1/1993 | Peterson |
| 5,190,032 A | 3/1993 | Zacoi |
| 5,259,835 A | 11/1993 | Clark |
| 5,306,236 A | 4/1994 | Blumenfeld et al. |
| 5,336,219 A | 8/1994 | Krantz |
| 5,377,695 A | 1/1995 | An Haack |
| 5,514,155 A | 5/1996 | Daneshvar |
| 5,533,519 A | 7/1996 | Radke et al. |
| 5,562,705 A | 10/1996 | Whiteford |
| 5,665,108 A | 9/1997 | Galindo |
| 5,725,507 A | 3/1998 | Petrick |
| 5,788,660 A | 8/1998 | Resnik |
| 5,823,983 A | 10/1998 | Rosofsky |
| 5,843,123 A | 12/1998 | Brazeau |
| 5,910,125 A | 6/1999 | Cummings |
| 6,007,564 A | 12/1999 | Haverstock |
| 6,033,654 A | 3/2000 | Stedronsky et al. |
| 6,074,965 A | 6/2000 | Bodenschatz et al. |
| 6,126,615 A | 10/2000 | Allen et al. |
| 6,176,868 B1 | 1/2001 | Detour |
| 6,194,629 B1 | 2/2001 | Bernhard |
| 6,629,949 B1 | 10/2003 | Douglas |
| 6,689,100 B2 | 2/2004 | Connelly et al. |
| 6,726,706 B2 | 4/2004 | Dominguez |
| 7,066,182 B1 | 6/2006 | Dunshee |
| 7,361,185 B2 | 4/2008 | O'Malley et al. |
| 7,455,681 B2 | 11/2008 | Wilke et al. |
| 7,511,185 B2 | 3/2009 | Lesner |
| 7,641,682 B2 | 1/2010 | Palmaz et al. |
| 7,645,285 B2 | 1/2010 | Cosgrove et al. |
| 7,799,042 B2 | 9/2010 | Williamson et al. |
| 8,246,590 B2 | 8/2012 | Hu et al. |
| 8,313,508 B2 | 11/2012 | Belson et al. |
| 8,323,313 B1 | 12/2012 | Belson et al. |
| 8,439,945 B2 | 5/2013 | Belson et al. |
| 8,592,640 B2 | 11/2013 | Zepeda et al. |
| 8,663,275 B2 | 3/2014 | O'Malley et al. |
| 9,008,784 B2 | 4/2015 | Chan et al. |
| 9,050,086 B2 | 6/2015 | Belson et al. |
| 9,089,328 B2 | 7/2015 | Belson et al. |
| 9,179,914 B2 | 11/2015 | Belson et al. |
| 9,248,049 B2 | 2/2016 | Gurtner |
| 9,271,858 B2 | 3/2016 | Ben-Meir et al. |
| 9,474,529 B2 | 10/2016 | Belson et al. |
| 9,554,799 B2 | 1/2017 | Belson et al. |
| 9,554,800 B2 | 1/2017 | Belson et al. |
| 9,561,034 B2 | 2/2017 | Belson et al. |
| 9,642,621 B2 | 5/2017 | Belson et al. |
| 9,642,622 B2 | 5/2017 | Belson et al. |
| 10,010,710 B2 | 7/2018 | Belson et al. |
| 10,123,800 B2 | 11/2018 | Belson et al. |
| 10,123,801 B2 | 11/2018 | Belson et al. |
| 10,456,136 B2 | 10/2019 | Belson et al. |
| 2002/0082668 A1 | 6/2002 | Ingman |

(56) References Cited

U.S. PATENT DOCUMENTS

| | | |
|---|---|---|
| 2002/0099315 A1 | 7/2002 | Lesner |
| 2003/0065294 A1 | 4/2003 | Pickup |
| 2003/0108352 A1 | 6/2003 | Hellman |
| 2003/0120198 A1 | 6/2003 | Barkell et al. |
| 2003/0163160 A1 | 8/2003 | O'Malley et al. |
| 2003/0220596 A1 | 11/2003 | Dunshee |
| 2004/0072964 A1 | 4/2004 | Udding et al. |
| 2004/0106904 A1 | 6/2004 | Gonnelli et al. |
| 2004/0204740 A1 | 10/2004 | Weiser |
| 2004/0210176 A1 | 10/2004 | Diana |
| 2004/0260234 A1 | 12/2004 | Srinivasan et al. |
| 2005/0020956 A1 | 1/2005 | Lesner |
| 2005/0020957 A1 | 1/2005 | Lesner |
| 2005/0070956 A1 | 3/2005 | Rousseau |
| 2005/0080453 A1 | 4/2005 | Lesner et al. |
| 2005/0085757 A1 | 4/2005 | Santanello |
| 2005/0153090 A1 | 7/2005 | Marchitto et al. |
| 2005/0234485 A1 | 10/2005 | Seegert et al. |
| 2005/0277959 A1 | 12/2005 | Cosgrove et al. |
| 2005/0284801 A1 | 12/2005 | Tacklind |
| 2006/0030886 A1 | 2/2006 | Clark |
| 2006/0122522 A1 | 6/2006 | Chavan |
| 2006/0200198 A1 | 9/2006 | Riskin et al. |
| 2006/0259033 A1 | 11/2006 | Nesbitt |
| 2007/0026078 A1 | 2/2007 | Almarsson et al. |
| 2007/0038247 A1 | 2/2007 | Lesner et al. |
| 2007/0078366 A1 | 4/2007 | Haggstrom et al. |
| 2007/0088339 A1 | 4/2007 | Luchetti et al. |
| 2007/0106277 A1 | 5/2007 | Hood |
| 2007/0141130 A1 | 6/2007 | Villanueva et al. |
| 2007/0179419 A1 | 8/2007 | Simpson |
| 2007/0185432 A1 | 8/2007 | Etheredge |
| 2007/0260278 A1 | 11/2007 | Wheeler et al. |
| 2008/0033334 A1 | 2/2008 | Gurtner et al. |
| 2008/0069855 A1 | 3/2008 | Bonutti |
| 2008/0081951 A1 | 4/2008 | Frasier et al. |
| 2008/0103550 A1 | 5/2008 | Wenzel et al. |
| 2008/0114396 A1 | 5/2008 | Cory et al. |
| 2008/0147115 A1 | 6/2008 | O'Malley et al. |
| 2008/0161731 A1 | 7/2008 | Woods et al. |
| 2008/0228219 A1 | 9/2008 | Weiser |
| 2008/0262543 A1* | 10/2008 | Bangera ............ A61B 17/0401 606/232 |
| 2008/0287864 A1 | 11/2008 | Rosenberg |
| 2009/0062531 A1 | 3/2009 | Kanda |
| 2009/0099496 A1 | 4/2009 | Heegaard et al. |
| 2009/0036922 A1 | 5/2009 | Riskin et al. |
| 2009/0149869 A1 | 6/2009 | Lhun |
| 2009/0158131 A1 | 6/2009 | Choi et al. |
| 2009/0162531 A1 | 6/2009 | Nesbitt |
| 2009/0177225 A1 | 7/2009 | Nunez et al. |
| 2009/0177227 A1 | 7/2009 | Warren |
| 2009/0264709 A1 | 10/2009 | Blurton et al. |
| 2009/0299255 A1 | 12/2009 | Kazala, Jr. et al. |
| 2009/0299257 A1 | 12/2009 | Long et al. |
| 2009/0299303 A1 | 12/2009 | Seegert |
| 2010/0036209 A1 | 2/2010 | Ferren et al. |
| 2010/0100022 A1 | 4/2010 | Greener et al. |
| 2010/0121286 A1 | 5/2010 | Locke et al. |
| 2010/0228287 A1 | 9/2010 | Jeekel et al. |
| 2010/0280545 A1 | 11/2010 | Fridman |
| 2011/0077667 A1 | 3/2011 | Singhatat et al. |
| 2011/0106026 A1 | 5/2011 | Wu |
| 2011/0118698 A1 | 5/2011 | Eckhoff et al. |
| 2011/0144470 A1 | 6/2011 | Mazar et al. |
| 2012/0016410 A1 | 1/2012 | Belson et al. |
| 2012/0029266 A1 | 2/2012 | Holmes et al. |
| 2012/0046691 A1 | 2/2012 | Belson et al. |
| 2012/0095502 A1 | 4/2012 | Bargon et al. |
| 2012/0116279 A1 | 5/2012 | Munro et al. |
| 2012/0116485 A1 | 5/2012 | Burgmann |
| 2012/0203273 A1 | 8/2012 | Riskin et al. |
| 2012/0221044 A1 | 8/2012 | Archibald et al. |
| 2012/0226214 A1 | 9/2012 | Gurtner et al. |
| 2012/0232587 A1 | 9/2012 | Burke et al. |
| 2013/0066365 A1 | 3/2013 | Belson et al. |
| 2013/0072969 A1 | 3/2013 | Zhang |
| 2013/0108352 A1 | 5/2013 | Ruiz, Sr. et al. |
| 2013/0178897 A1 | 7/2013 | Wu et al. |
| 2013/0267928 A1 | 10/2013 | Imran et al. |
| 2013/0281885 A1 | 10/2013 | Rowbottom et al. |
| 2013/0281981 A1 | 10/2013 | Shamir |
| 2013/0282049 A1 | 10/2013 | Peterson et al. |
| 2013/0296930 A1 | 11/2013 | Belson et al. |
| 2013/0331757 A1 | 12/2013 | Belson |
| 2014/0074156 A1 | 3/2014 | Belson et al. |
| 2014/0171849 A1 | 6/2014 | Fischell et al. |
| 2014/0222070 A1 | 8/2014 | Belson et al. |
| 2014/0228712 A1 | 8/2014 | Elliott et al. |
| 2014/0278229 A1 | 9/2014 | Hong et al. |
| 2014/0316323 A1 | 10/2014 | Kanevsky |
| 2015/0045700 A1 | 2/2015 | Cavanagh et al. |
| 2015/0051530 A1* | 2/2015 | Noda ................ A61B 17/085 602/41 |
| 2015/0105423 A1 | 4/2015 | Haudenschild et al. |
| 2015/0148653 A1 | 5/2015 | Fleig et al. |
| 2015/0209563 A1 | 7/2015 | Amir |
| 2015/0216527 A1 | 8/2015 | Belson et al. |
| 2015/0309535 A1 | 10/2015 | Connor et al. |
| 2015/0313593 A1 | 11/2015 | Patenaude et al. |
| 2015/0351690 A1 | 12/2015 | Toth et al. |
| 2016/0007909 A1 | 1/2016 | Singh et al. |
| 2016/0058998 A1 | 3/2016 | Skiba |
| 2016/0095597 A1 | 4/2016 | Belson et al. |
| 2016/0106931 A1 | 4/2016 | Belson et al. |
| 2016/0114146 A1 | 4/2016 | Belson et al. |
| 2016/0202755 A1 | 7/2016 | Connor |
| 2016/0206311 A1 | 7/2016 | Belson et al. |
| 2016/0206312 A1 | 7/2016 | Belson et al. |
| 2016/0206313 A1 | 7/2016 | Belson et al. |
| 2016/0213924 A1 | 7/2016 | Coleman et al. |
| 2016/0220175 A1 | 8/2016 | Tam et al. |
| 2016/0220252 A1 | 8/2016 | Belson et al. |
| 2016/0242646 A1 | 8/2016 | Obma |
| 2016/0249924 A1 | 9/2016 | Belson et al. |
| 2016/0296149 A1 | 10/2016 | Polsky et al. |
| 2016/0302721 A1 | 10/2016 | Wiedenhoefer et al. |
| 2016/0310140 A1 | 10/2016 | Belson et al. |
| 2017/0035422 A1 | 2/2017 | Belson et al. |
| 2017/0042541 A1 | 2/2017 | Belson et al. |
| 2017/0143341 A1 | 5/2017 | Belson et al. |
| 2017/0156664 A1 | 6/2017 | Belson et al. |
| 2019/0060128 A1 | 2/2019 | Belson |

FOREIGN PATENT DOCUMENTS

| | | |
|---|---|---|
| CN | 1524507 A | 9/2004 |
| CN | 1234327 C | 1/2006 |
| CN | 101563113 A | 10/2009 |
| CN | 101801456 A | 8/2010 |
| CN | 01938944 A | 1/2011 |
| CN | 202537562 U | 11/2012 |
| CN | 102946812 A | 2/2013 |
| CN | 104755033 A | 7/2015 |
| CN | 104825200 A | 8/2015 |
| EP | 1600108 A2 | 11/2005 |
| GB | 1401877 | 8/1975 |
| JP | S4868094 A | 9/1973 |
| JP | S5094788 | 7/1975 |
| JP | S5223497 | 6/1977 |
| JP | S62243557 | 10/1987 |
| JP | H07502913 A | 3/1995 |
| JP | 2001149485 A | 6/2001 |
| JP | 2005512678 A | 5/2005 |
| JP | 2005532134 A | 10/2005 |
| JP | 2010504835 A | 2/2010 |
| JP | 2013515417 A | 5/2013 |
| JP | 2013538603 A | 10/2013 |
| KR | 200354734 Y1 | 6/2004 |
| KR | 2020140001338 U | 3/2014 |
| WO | 8401805 A1 | 5/1984 |
| WO | 9629013 A1 | 9/1996 |
| WO | 03053296 A1 | 7/2003 |
| WO | 2006124671 A2 | 11/2006 |

(56) References Cited

FOREIGN PATENT DOCUMENTS

| WO | 2007004603 A1 | 1/2007 |
|---|---|---|
| WO | 2007044647 A2 | 4/2007 |
| WO | 2008019051 A2 | 2/2008 |
| WO | 2008060532 A2 | 5/2008 |
| WO | 2009066116 A1 | 5/2009 |
| WO | 2011019859 A2 | 2/2011 |
| WO | 2011019859 A3 | 4/2011 |
| WO | 2011043786 A1 | 4/2011 |
| WO | 2011139912 A1 | 11/2011 |
| WO | 2011159623 A1 | 12/2011 |
| WO | 2013067024 A1 | 5/2013 |
| WO | 2014066879 A2 | 5/2014 |
| WO | 2014070922 A1 | 5/2014 |
| WO | 2015012887 A1 | 1/2015 |
| WO | 2015103556 A1 | 7/2015 |
| WO | 2015168165 A1 | 11/2015 |
| WO | 2017027075 A1 | 2/2017 |
| WO | 2017044120 A1 | 3/2017 |
| WO | 2017181059 A1 | 10/2017 |
| WO | 2017184825 A1 | 10/2017 |
| WO | 2018081795 | 5/2018 |

OTHER PUBLICATIONS

Office action dated Oct. 23, 2015 for U.S. Appl. No. 13/665,160.
European search report and opinion dated Jan. 7, 2014 for EP Application No. 11778067.6.
European search report and opinion dated Jan. 7, 2014 for EP Application No. 11796253.0.
European search report and opinion dated Apr. 29, 2015 for EP Application No. 10822334.8.
European search report and opinion dated Jul. 12, 2016 for EP Application No. 13851258.
European search report and written opinion dated Aug. 12, 2015 for EP Application No. 12844746.3.
Hasson, et al. A new sutureless technique for skin closure. Arch Surg. Jan. 1976;111 (1):83-4.
International search report and written opinion dated Jan. 12, 2016 for PCT Application No. US2015/049671.
International search report and written opinion dated Feb. 6, 2014 for PCT/US2013/067563.
International search report and written opinion dated Mar. 19, 2013 for PCT/US2012/062820.
International search report and written opinion dated Apr. 29, 2015 for PCT/US2015/010188.
International search report and written opinion dated Jul. 29, 2011 for PCT/US2011/034649.
International search report and written opinion dated Jul. 30, 2010 for PCT/US2010/000430.
International search report and written opinion dated Sep. 10, 2014 for PCT/US2014/016587.
International search report and written opinion dated Sep. 30, 2015 for PCT Application No. US2015/28066.
International search report and written opinion dated Oct. 21, 2011 for PCT Application No. US11/40213.
K984204, 510(k) Premarket Notification Summary, Silverlon TM Direct Pressure Wound Closure Strip, May 19, 2007.
Merriam-Webster Dictionary. Definition of "lateral". Http://www.merriamwebster.com/dictionary/lateral. Accessed on May 5, 2016.
Notice of allowance dated Jan. 17, 2013 for U.S. Appl. No. 13/096,602.
Notice of allowance dated Feb. 10, 2015 for U.S. Appl. No. 14/180,524.
Notice of allowance dated Jun. 21, 2016 for U.S. Appl. No. 15/081,526.
Notice of allowance dated Sep. 17, 2012 for U.S. Appl. No. 13/286,378.
Notice of allowance dated Sep. 20, 2012 for U.S. Appl. No. 13/286,757.
Notice of allowance dated Sep. 22, 2015 for U.S. Appl. No. 13/414,176.
Notice of allowance dated Dec. 19, 2014 for U.S. Appl. No. 14/180,564.
Office action dated Feb. 26, 2015 for U.S. Appl. No. 13/414,176.
Office action dated Mar. 4, 2016 for U.S. Appl. No. 13/874,046.
Office action dated Mar. 21, 2012 for U.S. Appl. No. 13/286,378.
Office action dated Mar. 21, 2014 for U.S. Appl. No. 13/414,176.
Office action dated Mar. 22, 2012 for U.S. Appl. No. 13/286,757.
Office action dated Apr. 7, 2015 for U.S. Appl. No. 13/685,909.
Office action dated May 2, 2012 for U.S. Appl. No. 13/096,602.
Office action dated May 3, 2016 for U.S. Appl. No. 13/665,160.
Office action dated May 11, 2016 for U.S. Appl. No. 15/081,595.
Office action dated May 12, 2016 for U.S. Appl. No. 15/081,550.
Office action dated May 26, 2016 for U.S. Appl. No. 15/081,526.
Office action dated May 31, 2016 for U.S. Appl. No. 15/096,083.
Office action dated Jun. 5, 2015 for U.S. Appl. No. 13/874,046.
Office action dated Jun. 17, 2014 for U.S. Appl. No. 13/414,176.
Office action dated Jun. 17, 2016 for U.S. Appl. No. 15/130,149.
Office action dated Jul. 20, 2016 for U.S. Appl. No. 15/130,764.
Office action dated Jul. 23, 2012 for U.S. Appl. No. 13/286,378.
Office action dated Jul. 23, 2012 for U.S. Appl. No. 13/286,757.
Office action dated Aug. 18, 2014 for U.S. Appl. No. 14/180,564.
Office action dated Aug. 28, 2014 for U.S. Appl. No. 14/180,524.
Office action dated Sep. 19, 2014 for U.S. Appl. No. 13/685,909.
Office action dated Oct. 14, 2015 for U.S. Appl. No. 13/685,909.
Office action dated Dec. 29, 2014 for U.S. Appl. No. 13/685,909.
Zip® Surgical Skin Closure. Fast, non-invasive alternative to staples, sutures and glue. Accessed Aug. 17, 2016. http://www.ziplinemedical.com/products/zip-surgical-skin-closure/.
International search report and written opinion dated Aug. 30, 2016 for PCT/US2016/028297.
Office Action dated Nov. 22, 2017 for U.S. Appl. No. 15/130,764.
Office Action dated Nov. 28, 2017 for U.S. Appl. No. 15/442,382.
PCT/US2017/059286 International Search Report and Written Opinion dated Mar. 6, 2018.
U.S. Appl. No. 14/851,059 Notice of Allowance dated Mar. 14, 2018.
dictionary.com definition of fixed, accessed on Sep. 13, 2017, http://www.dictionary.com/browse/fixed.
European search report and opinion dated Feb. 17, 2017 for EP Application No. 140829202.
European search report with written opinion dated Jul. 12, 2016 for EP13851258.
Extended European search report and opinion dated 07127/2017 for EP Application No. 14889182.
International search report with written opinion dated Jul. 14, 2017 for PCT/US2017/027695.
International search report with written opinion dated Jul. 18, 2017 for PCT/US2017/028537.
International search report with written opinion dated Aug. 30, 2016 for PCT/US2016/028297.
Merriam-webster definition of integral, accessed on Sep. 13, 2017, https://www.merriamwebster.com/dictionary/integral.
Notice of allowance dated Feb. 21, 2017 for U.S. Appl. No. 14/625,366.
Notice of allowance dated Feb. 23, 2016 for U.S. Appl. No. 15/081,595.
Notice of allowance dated Dec. 19, 2016 for U.S. Appl. No. 15/130,149.
Office action dated Jun. 1, 2017 for U.S. Appl. No. 15/442,382.
Office action dated Jun. 2, 2017 for U.S. Appl. No. 13/665,160.
Office action dated Jul. 27, 2017 for U.S. Appl. No. 14/851,059.
Office action dated Aug. 24, 2017 for U.S. Appl. No. 14/958,803.
Office Action dated Sep. 22, 2017 for U.S. Appl. No. 13/665,160.
Office Action dated Sep. 26, 2017 for U.S. Appl. No. 13/685,909.
Office Action dated Oct. 5, 2017 for U.S. Appl. No. 14/958,818.
Office action dated Feb. 1, 2017 for U.S. Appl. No. 15/130,764.
Notice of allowance dated Sep. 30, 2016 for U.S. Appl. No. 15/130,149.
Notice of allowance dated Oct. 5, 2016 for U.S. Appl. No. 15/096,083.
Notice of allowance dated Oct. 14, 2016 for U.S. Appl. No. 15/081,550.

(56) References Cited

OTHER PUBLICATIONS

Office action dated Nov. 17, 2016 for U.S. Appl. No. 15/081,595.
Office action dated Dec. 1, 2016 for U.S. Appl. No. 13/665,160.
Notice of Allowance dated Jun. 15, 2018 for U.S. Appl. No. 13/665,160.
Notice of Allowance dated Jun. 20, 2018 for U.S. Appl. No. 15/130,764.
Notice of Allowance dated Aug. 9, 2018 for U.S. Appl. No. 14/851,059.
Thakral; et al., "Electrical stimulation to accelerate wound healing", CoAction, 2013, 4:22061, 1-9.
U.S. Appl. No. 14/958,803 Notice of Allowance dated Apr. 4, 2018.
U.S. Appl. No. 14/958,803 Notice of Allowance dated May 11, 2018.
Ann; Davis et al., "Effect of Surgical Incision Closure Device on Skin Perfusion Following Total Ankle Arthroplasty", UFHealth, 2017, Poster.
Bauback; Safa et al., "In Vivo Efficacy Study Showing Comparative Advantage of Bacterial Infection Prevention with Zip-type Skin Closure Device vs. Subcuticular Sutures", Cureus, Aug. 4, 2018, 3102,1-11.
Cody; C. Wyles et al., "Running Subcuticular Closure Enables the Most Robust Perfusion After TKA: A Randomized Clinical Trial", Clinical Orthopaedics and Related Research, Springer, Mar. 3, 2015, 1-10.
Kemal; Levi et al., "Mechanics of Wound Closure: Emerging Tape-Based Wound Closure Technology vs. Traditional Methods", Cure us, Oct. 12, 2016, 827, 1-5.
U.S. Appl. No. 13/685,909 Office Action dated May 1, 2018.
Office action dated Nov. 2, 2018 for U.S. Appl. No. 15/442,382.
Office action dated Feb. 25, 2019 for U.S. Appl. No. 15/369,293.
Office action dated Mar. 26, 2019 for U.S. Appl. No. 16/132,736.

\* cited by examiner

Wound closure device layout

Wound closure device cross-section

Therapy/Sensor device between adhesive and skin

Therapy/Sensor device embedded in adhesive

Therapy/Sensor device between adhesive and substrate

Therapy/Sensor device between substrate and load-distributing element

Therapy/Sensor device on top of substrate or load-distributing element

Therapy/Sensor device placed into pocket within the adhesive

Therapy/Sensor device placed into pocket between adhesive and substrate

Therapy/Sensor device placed into pocket between substrate and load-distributing element Wound closure device with sensor/therapeutic
element attached to top of device

INSTRUMENTED WOUND CLOSURE DEVICE

CROSS-REFERENCE

The present application is a divisional of Ser. No. 15/201,088, filed Jul. 1, 2016, which is a continuation of PCT International Application No. PCT/US2015/010188, filed Jan. 5, 2015, which claims the benefit of U.S. Provisional Application No. 61/964,477, filed Jan. 5, 2014. The entire disclosure contents of these applications are herewith incorporated by reference into the present application.

BACKGROUND

The present application relates to medical systems, devices, and methods. In particular, the present application relates to the construction, use, and function of surgical incision closure devices with integrated therapeutic and/or sensor properties.

SUMMARY

Medical devices, systems, and methods which incorporate therapeutic and/or sensory capabilities into a wound closure device are disclosed herein.

The inventors of the present application have previously disclosed inventions relating to surgical skin closure. Such skin closure appliances are described, for example, in U.S. Provisional Application Nos. 61/958,254 and 61/958,259, both filed Jul. 24, 2013, and U.S. patent application Ser. No. 14/180,524, filed Feb. 14, 2014, the contents of which are incorporated herein by reference. As described, an adhesive patch may be placed over a patient's skin at a site where it is desired to form a surgical incision. After the patch is placed, an incision is formed along an axial line extending through the middle of the patch. After it is formed, the incision can be opened to perform a desired procedure, and after the procedure is completed, the incision may be closed by drawing the inner edges of the panels together with a clip, zipper, ratchet, strap, or other closure member(s). Such surgical closure devices are meant to improve healing and reduce scarring from the incision.

Topical sensors, including those measuring motion, acceleration, stress/strain, temperature, pressure, oxygen saturation and tension, $CO_2$ tension, moisture and other parameters, are well known in the art and the medical device market. However, incorporation of such sensors and functionality into wound closure devices and/or use in conjunction with post-operative physical therapy is yet to be available in the marketplace. In addition, delivery of therapeutic capabilities, including delivery of heat, light (including infrared, visible and ultraviolet), electrical signals, motion (e.g., vibration), and pressure, are well known in the art and the medical device market. However, incorporation of such properties into a wound closure device and/or use in conjunction with post-operative physical therapy is yet to be available in the marketplace. Aspects of the present disclosure provide wound or incision closure appliances and methods of use which incorporate at least some of the aforementioned capabilities.

Aspects of the present disclosure provide wound or incision closure apparatuses comprising a first panel for placement laterally adjacent a first lateral side of a wound or incision, a second panel for placement laterally adjacent a second lateral side of the wound or incision, and a sensory or therapeutic element disposed adjacent or integrated into one or more of the first or second panels. The first panel may comprise a first bottom adhesive layer, a first medial substrate layer, and a first upper load distribution layer. Similarly, the second panel may comprise a second bottom adhesive layer, a second medial substrate layer, and a second upper load distribution layer connectable to the first upper load distribution layer, for example through one or more straps and strap ratchets. The different layers of the panels may be constructed of a variety of materials as described further below.

The sensory or therapeutic element may be disposed adjacent or integrated into one or more of the first bottom adhesive layer, the second bottom adhesive layer, the first medial substrate layer, the second medial substrate layer, the first upper load distribution layer, or the second upper load distribution layer. The sensory or therapeutic element may be disposed within a pocket between two or more of the layers of one or more of the first or second panels. The first or second panels may have an access traversing one or more of the layers to allow access to the pocket.

The sensory or therapeutic element may be configured to be in communication, such as wireless communication (e.g., Bluetooth, Bluetooth LE, WiFi, IR signal(s), and the like) with a receiving device external of the wound or incision closure apparatus. The receiving device may comprise a workstation, a personal computer, a laptop computer, a tablet computer, a smartphone, a wearable computer, a dedicated receiver, or the like.

The sensory or therapeutic element may comprise one or more of a thermometer, a motion sensor, a chemical sensor, a pressure sensor, a therapy delivery element, or other sensor. A motion sensor may, for example, comprise one or more of a strain gauge, an electromechanical sensor, an electromagnetic sensor, an accelerometer, an optical sensor, or other motion sensor. A chemical sensor may, for example, be configured to measure one or more of blood composition, transcutaneous oxygen, transcutaneous carbon dioxide, glucose levels, or pH. A therapy delivery element may, for example, comprise one or more of a light source for phototherapy, a mechanical vibration element, an ultrasound source, a drug delivery element, a heating element, a cooling element, an electrifying element, or an ultrasound source.

Aspects of the present disclosure also provide methods of treating a wound or incision. A first panel of a wound or incision closure apparatus may be adhered adjacent a first lateral side of the wound or incision. A second panel of the closure apparatus may be adhered adjacent a second lateral side of the wound or incision. The first and second panels may be drawn laterally together to draw the first and second lateral sides of the wound or incision together. A physiological parameter(s) may be sensed with a therapeutic or sensory element disposed on or within one or more of the first or second panels. The therapeutic or sensory element may sense the physiological parameter(s) intermittently (e.g., at the discretion of the user such as according to a schedule) and/or continuously (including at closely timed intervals, or once or a set number of times every one or more hours, one or more minutes, or one or more seconds). The physiological parameter(s) may comprise, for example, one or more of temperature, motion, moisture, pressure, the concentration of a physiological marker, pH, oxygen levels, carbon dioxide levels, or glucose levels, to name a few.

The method may further comprise a step of providing a therapy to patient with the therapeutic or sensory device. The therapy may comprise one or more of phototherapy, vibration therapy, ultrasound therapy, drug delivery, heat therapy, cooling therapy, or electrical therapy, to name a few.

The method may further comprise a step of transmitting the sensed physiological parameter(s) to an external receiving device. The transmission may be in real time with the sensing or detection of the physiological parameter(s) by the therapeutic or sensory device. The external receiving device may comprise one or more of a workstation, a personal computer, a laptop computer, a tablet computer, a smartphone, a wearable computer, or a dedicated receiver, to name a few.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

DETAILED DESCRIPTION

The present disclosure relates to wound closure devices incorporating therapeutic and/or sensory capabilities and their methods of use.

Incorporation of therapeutic and/or sensory capabilities.

Figure 1:
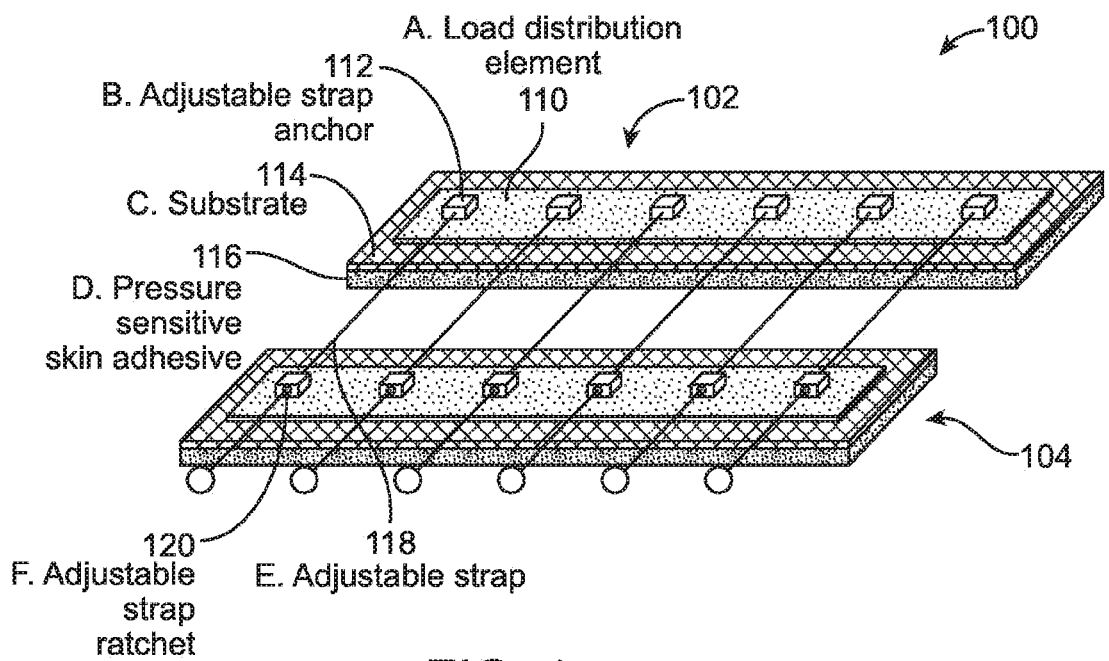
FIG. 1 shows a perspective view of a wound closure appliance, according to many embodiments.
Figure 2:
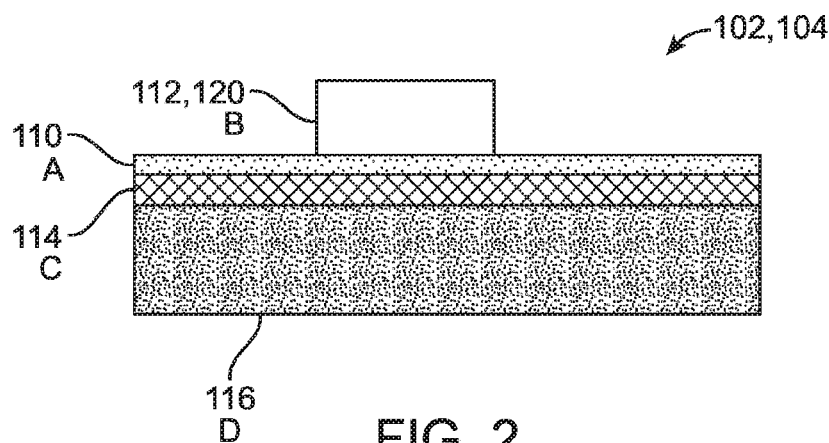
FIG. 2 shows a cross-sectional view of a panel of the wound closure appliance of FIG. 1.
Figure 3:
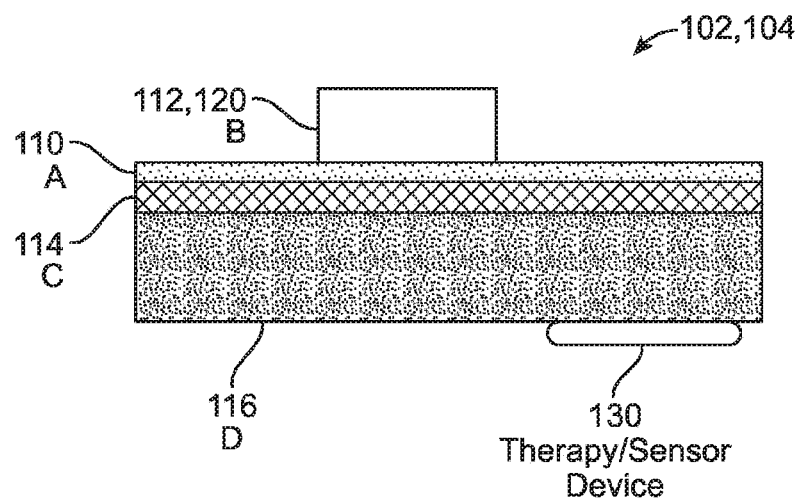
FIG. 3 shows a cross-sectional view of a panel of the wound closure appliance of FIG. 1 with a sensor or therapeutic element disposed below its adhesive layer and above skin, according to many embodiments.
Figure 4:
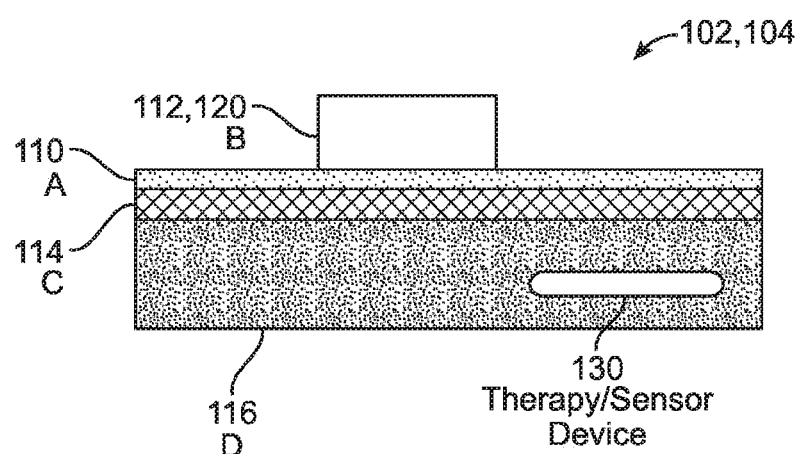
FIG. 4 shows a cross-sectional view of a panel of the wound closure appliance of FIG. 1 with a sensor or therapeutic element disposed within its adhesive layer, according to many embodiments.
Figure 5:
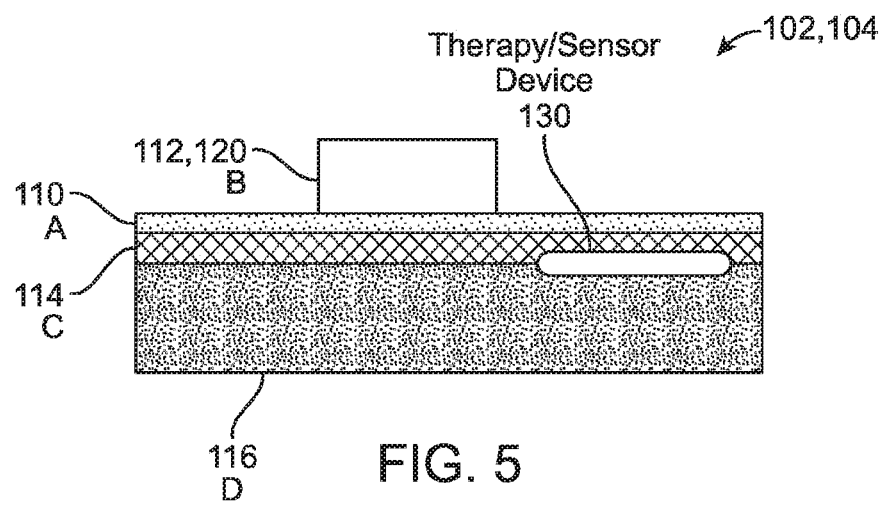
FIG. 5 shows a cross-sectional view of a panel of the wound closure appliance of FIG. 1 with a sensor or therapeutic element disposed between its substrate and adhesive layers, according to many embodiments.

FIG. 1 shows the layout of a basic wound closure device 100. The wound closure device 100 may comprise a first panel 102 and a second panel 104. In use, the first and second panels 102, 104 may be arranged in parallel across the lateral sides of an incision before being drawn laterally together to close the incision and maintain its closure. FIG. 2 shows a cross-section view of one of the panels 102 or 104 of the device 100. The device 100 may comprise multiple layers, including load distributions elements 100 to more evenly distribute the forces applied to maintain a wound or incision closed, adjustable anchor strap anchors 112 disposed on the upper surfaces of the first panel 102, substrate layers 114 below the load distribution elements 112, adhesive layers 116 which may be pressure sensitive, adjustable straps 118, and adjustable strap ratchets 120 over the top surface of the second panel 104. The adjustable straps 118 may connect the first and second panels 102 and 104 through adjustable strap anchors 112 and the adjustable strap ratchets 120. For example, an individual adjustable strap 118 may be pulled through the adjustable strap ratchet 120 to draw the panels 102 and 104 together. Further incision or wound closure apparatuses are described in U.S. Provisional Application Nos. 61/958,254 and 61/958,259, both filed Jul. 24, 2013, and U.S. patent application Ser. No. 14/180,524, filed Feb. 14, 2014, the contents of which are incorporated herein by reference. The incorporation of the therapeutic or sensory elements into the wound closure device may be achieved through one or more of the following methods.

The adhesive layer 116 may comprise a hydrophilic adhesive material such as one or more of a hydrocolloid, a hydrogel, an acrylic polymer, or poly (ethylene glycol). Hydrocolloid adhesives may have the benefit of being very tacky and able to absorb moisture and shedding skin cells. Thus, hydrocolloid adhesives may be particularly suited for long-term wear applications (e.g., up to 14 days). The substrate layer 114 may comprise one or more of rubber, latex, urethane, polyurethane, silicone, a thermoplastic elastomer (TPE), a woven fabric, or a spun fabric. The load distribution elements 112 may be made of similar materials as the substrate layer 114. The upper layers, the substrate layer 114 and the load distribution elements 112, will typically be flexible but stiff enough to securely close tissue and minimize disruption of the incision and surrounding tissue. The bottom layer 116 will typically be flexible and more elastic than the upper layers 114, 116 to maintain adhesion, minimize blistering, and otherwise reduce irritation.

One or more of the components of the incision closure appliances or incision closure appliance assemblies disclosed herein may be comprised of, be coated with, or otherwise incorporate one or more of an antifungal, antibacterial, antimicrobial, antiseptic, or medicated material. For example, such materials may be incorporated into the hydrocolloid adhesive layer, as another layer or coating between the skin and the adhesive layer (covering at least a portion of the adhesive layer), incorporated into the base assembly cover or at least its adhesive layer, etc. One or more wells, grooves, openings, pores, or similar structures may be provided on the device or apparatus components to facilitate such incorporation. In many embodiments, such materials may comprise one or more of silver, iodide, zinc, chlorine, copper, or natural materials such as tea tree oil as the active agent. Examples of such antifungal, antibacterial, antimicrobial, antiseptic, or medicated materials include, but are not limited to, the Acticoat™ family of materials available from Smith & Nephew plc of the U.K., the Acticoat® Moisture Control family of materials available from Smith & Nephew plc of the U.K., the Contreet® Foam family of materials available from Coloplast A/S of Denmark, the UrgoCell® Silver family of materials available from Urgo Limited of the U.K. (a subsidiary of Laboratoires URGO of France), the Contreet® Hydrocolloid family of materials available from Smith & Nephew plc of the U.K., the Aquacel® Ag family of materials available from ConvaTec Inc. of Skillman, N.J., the Silvercel® family of materials available from Kinetic Concepts, Inc. of San Antonio, Tex., Actisorb® Silver 220 available from Kinetic Concepts, Inc. of San Antonio, Tex., the Urgotul® SSD family of materials available from Urgo Limited of the U.K. (a subsidiary of Laboratoires URGO of France), the Inadine® family of materials available from Kinetic Concepts, Inc. of San Antonio, Tex., the Iodoflex® family of materials available from Smith & Nephew plc of the U.K., the Sorbsan Silver™ family of materials available from Aspen Medical Europe Ltd. of the U.K., the Polymem Silver® family of materials available from Ferris Mfg. Corp. of Burr Ridge, Ill., the Promogram™ family of materials available from Kinetic Concepts, Inc. of San Antonio, Tex., the Promogram Prisma™ family of materials available from Kinetic Concepts, Inc. of San Antonio, Tex., and the Arglaes® family of materials available from Medline Industries, Inc. of Mundelein, Ill. Components of the closure devices described in commonly owned U.S. Pat. Nos. 8,313,508, 8,323,313, and 8,439,945; U.S. Patent Publication No. 2013/0066365; and PCT application nos. US 2010/000430, US 2011/139912, US 2011/40213, US 2011/34649, and US 2013/067024 may also be comprised of, be coated with, or otherwise incorporate one or more of an antifungal, antibacterial, antimicrobial, antiseptic, or medicated material, including but not limited to one or more of the materials listed above.

In many embodiments, topical medicinal agents are incorporated directly into the wound closure appliances described herein. Because a wound closure device is often applied in close proximity to a wound or incision in need of medicinal protection, the incorporation of such medicines directly into the closure device may be beneficial. In wounds at risk of infection, incorporation of anti-microbial agents may be beneficial, for example. Anti-microbial agents may include antibiotic medicines as well as antiseptic metal ions and associated compounds which may include silver, iodine, copper, and chlorine, or natural materials such as tea tree oil. In wounds prone to fungus, medicinal agents such as zinc may be warranted, for example. Combinations of any of these agents may also be of benefit and thus may be incorporated into wound closure appliances.

Topical medicinal agents may be incorporated into the closure devices in a way to give the closure devices the ability to wick exudate away from the wound (e.g., to direct unwanted organisms away from the wound and/or prevent skin maceration), while keeping the wound sufficiently hydrated for improved healing.

Figure 6:
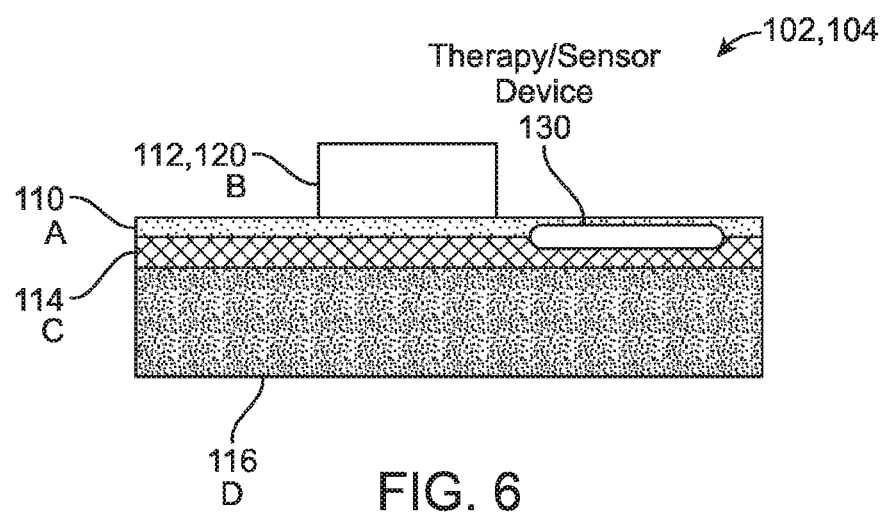
FIG. 6 shows a cross-sectional view of a panel of the wound closure appliance of FIG. 1 with a sensor or therapeutic element disposed between its force distribution structure and substrate layers, according to many embodiments.

One or more therapeutic or sensory element 130 may be embedded into the material of the panel 100 as shown in FIGS. 3, 4, 5 and 6. One or more therapeutic or sensory element 130 may be embedded the pressure-sensitive adhesive layer 116 of the device (FIG. 4) or attached to the bottom of said layer (FIG. 3), or in the laminate between the layers of the device 100 such as between the substrate layer 114 and the adhesive layer 116 (FIG. 5) and between the load distribution layer 110 and the substrate layer 114 (FIG. 6).

Figure 8:
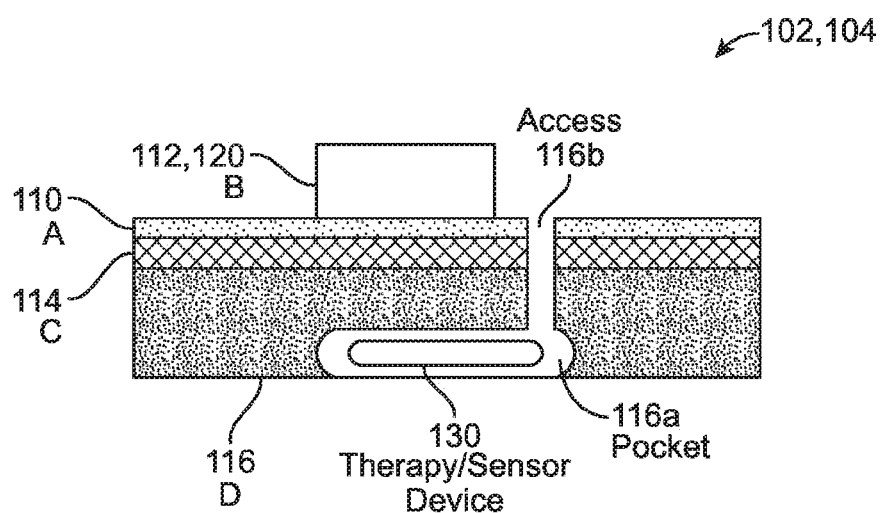
FIG. 8 shows a cross-sectional view of a panel of the wound closure appliance of FIG. 1 with a sensor or therapeutic element disposed within its adhesive layer and further provided with an accessible pocket for the sensor, according to many embodiments.
Figure 9:
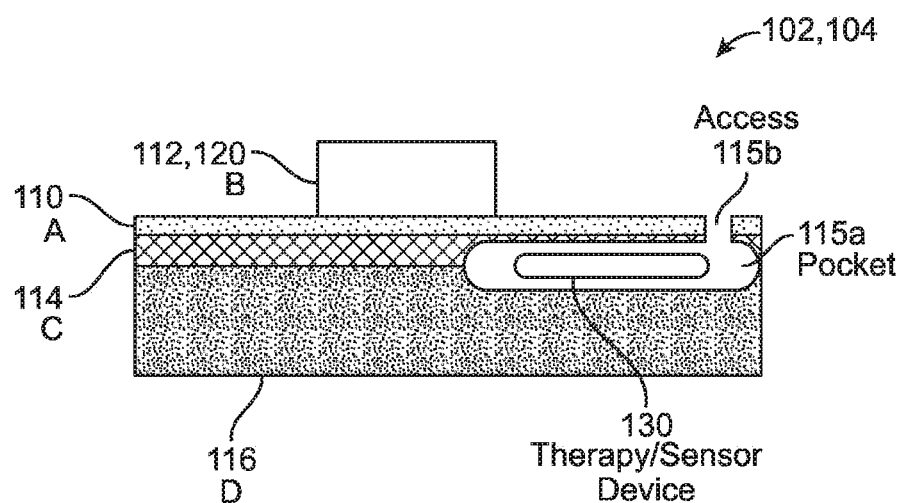
FIG. 9 shows a cross-sectional view of a panel of the wound closure appliance of FIG. 1 with a sensor or therapeutic element disposed between its substrate and adhesive layers, and further provided with an accessible pocket for the sensor or therapeutic element, according to many embodiments.
Figure 10:
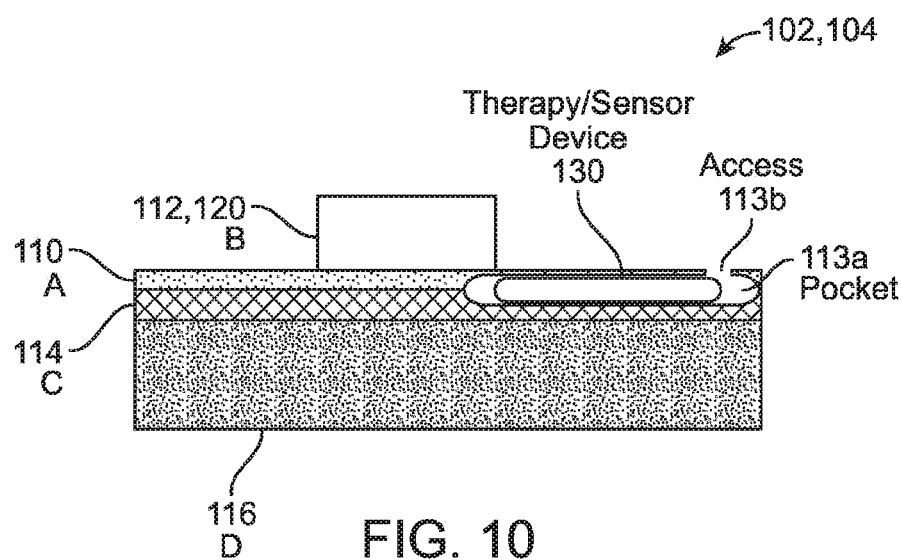
FIG. 10 shows a cross-sectional view of a panel of the wound closure appliance of FIG. 1 with a sensor or therapeutic element disposed between its force distribution structure and substrate layers, and further provided with an accessible pocket, according to many embodiments.

The therapeutic or sensory element(s) 130 may be embedded into a pocket created within one or more of the panels 102 or 104 as shown in FIGS. 8, 9 and 10. The therapeutic or sensory element(s) 130 may be incorporated into the device 100 by creating a pocket or envelope 116*a* within the adhesive layer 116 (FIG. 8), a pocket or envelope 115*a* between the adjoining substrate layer 114 and the adhesive layer 116 (e.g., between a monofilm or fabric of the substrate layer 104 and the pressure-sensitive skin adhesive layer 116; FIG. 9), or a pocket or envelope 113*a* between the adjoining load distribution element layer 110 and the substrate layer 114 (e.g., between the monofilm or fabric of the substrate layer 104 and closure mechanism of the load distribution layer 110; FIG. 10). Potentially, such pockets 116*a*, 115*a*, and/or 113*a* may have special skin windows made by special material (such as conductive material, material clear to specific wavelengths, etc.) Alternatively or in combination, such pockets 116*a*, 115*a*, and/or 113*a* may be accessible through accesses 116*b*, 115*b*, and/or 113*b*, respectively, through the layers of the panels 102 or 104 as shown in FIGS. 8, 9, and 10, respectively.

Figure 7:
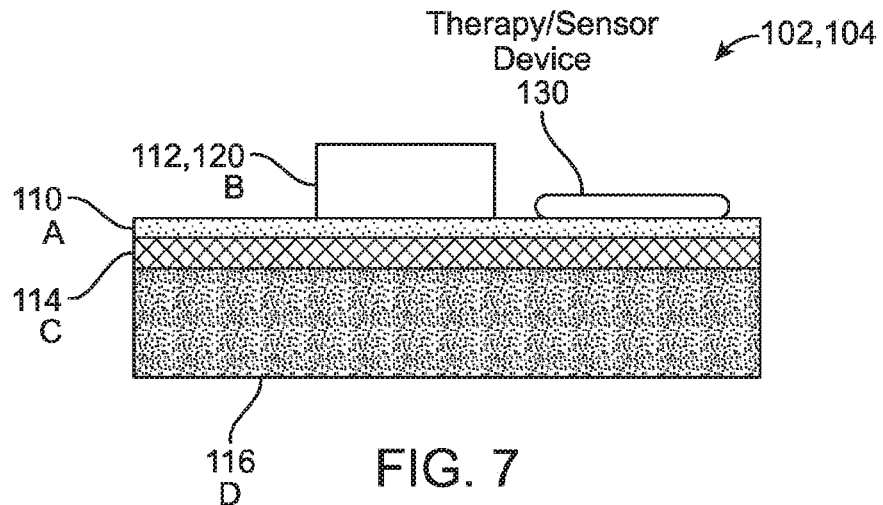
FIG. 7 shows a cross-sectional view of a panel of the wound closure appliance of FIG. 1 with a sensor or therapeutic element disposed over its force distribution structure layer, according to many embodiments.
Figure 11:
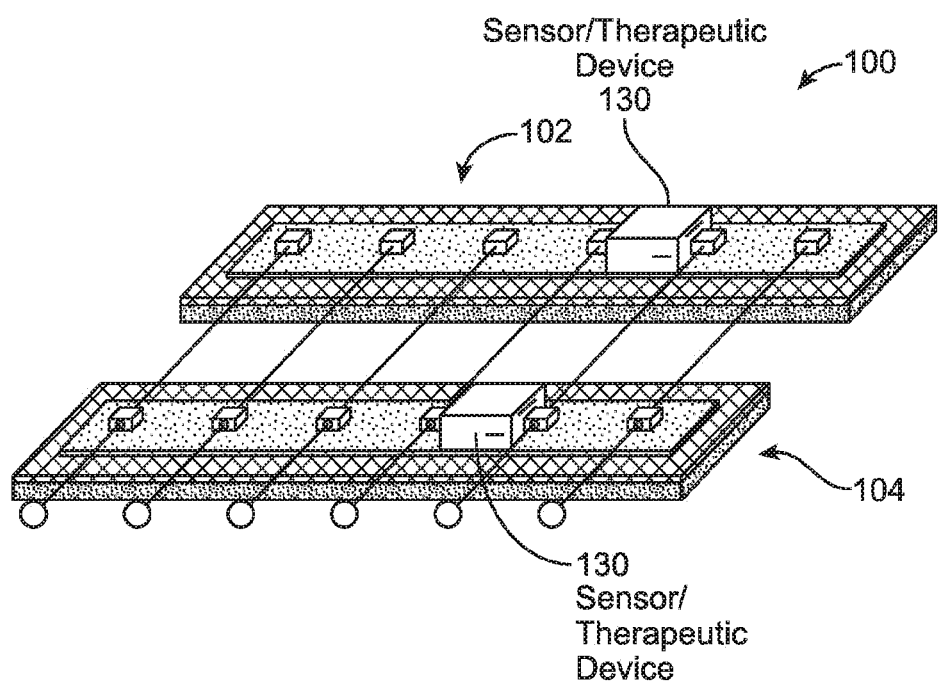
FIG. 11 shows a perspective view of the wound closure appliance of FIG. 1 with sensors or therapeutic elements disposed over its top surface, according to many embodiments.

The therapeutic or sensory element(s) 130 may be attached to the top or upper surfaces of the device 100 as shown in FIGS. 7 and 11. The element(s) 130 may be attached to the top of the device 100, either in a permanent (e.g. glued, stapled, sutured) or releasable (e.g., removable adhesive, hook-and-loop, snap, clip, button, or passive contact (e.g., held in place by another means, such as tape, additional bandage, elastic/compressive wrap, magnets)) manner.

Figure 12:
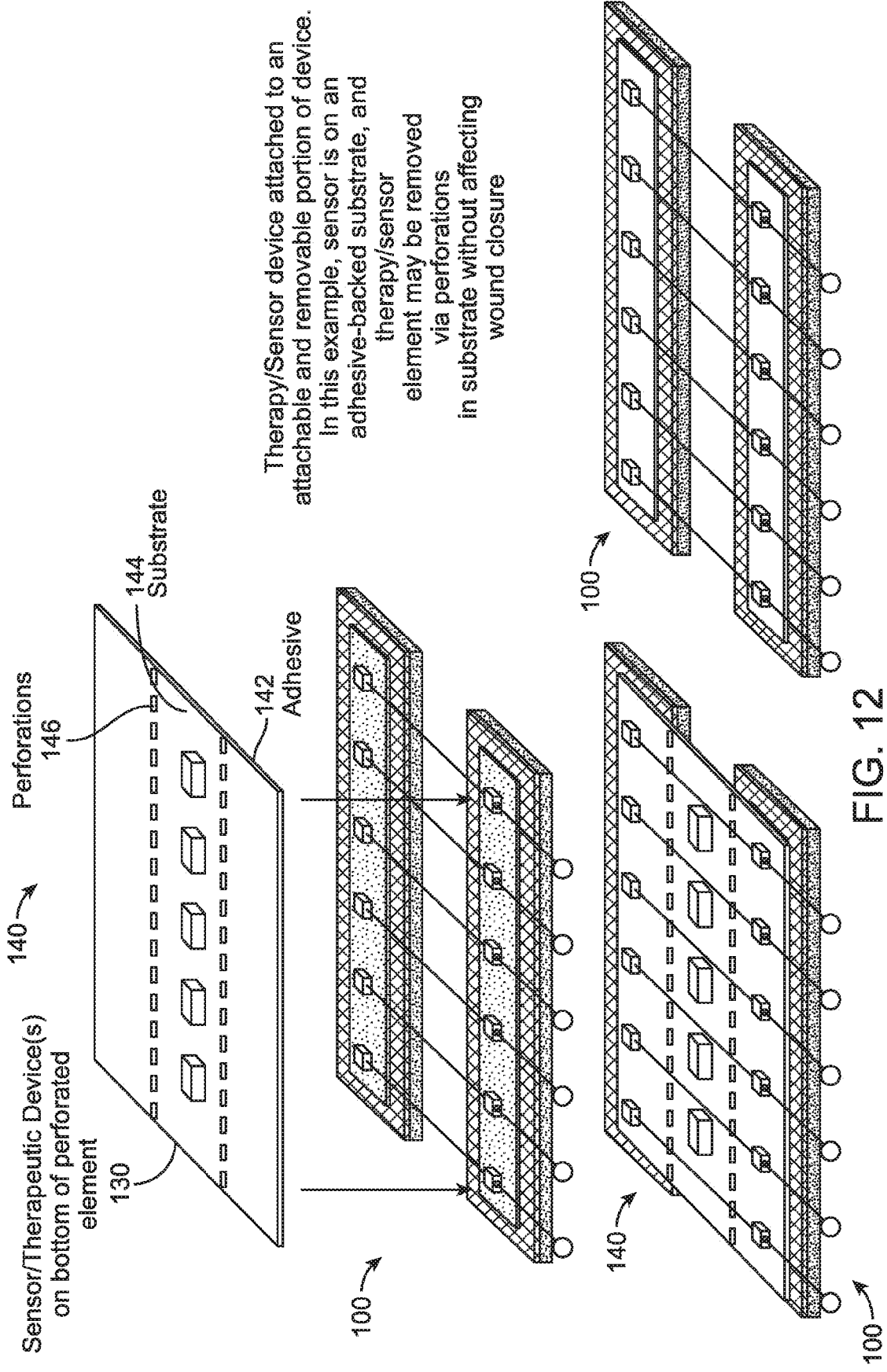
FIG. 12 shows a perspective view of the wound closure appliance of FIG. 1 and a cover sheet having one or more sensors or therapeutic elements incorporated thereon or therein, according to many embodiments.

The therapeutic or sensory element(s) 130 may be attached or embedded on a removable or attachable portion of device 100 as shown in FIG. 12. The element(s) 130 may be attached to a segment of the device 100 that is either attached at a different time than at the time of wound closure (e.g., 24 hours after closure), or removed from the device 100 before the entire device 100 is removed from the skin (e.g., removed (via perforations, hook-and-loop fasteners, etc.), so that the sensor or therapeutic element(s) 130 provides the most clinical utility at an appropriate time or for an appropriate duration. The manner of attachment or integration may, for example, place the sensor or therapeutic element(s) 130 directly over or in contact with the incision, which is generally in the center of the device 100 between the two adhesive strips or panels 102 and 104 along each side of the wound.

The therapeutic or sensory element(s) 130 may be attached to a patient regardless of the particularities of the wound closure mechanism. The element(s) 130 may be attached to the patient at the location of independent of the closure mechanism (e.g., adhesive closure device, staples, sutures), such that it can provide the same feedback as any element integrated into a closure mechanism. The element(s) 130 may also have utility for applications remote to the surgical incision, or where no incision is present at all, in order to guide physical therapy and recovery for both post-surgical and other non-surgical therapy.

Manners of Activation and/or Sensing.

The therapeutic or sensory element(s) 130 can be activated or can transmit sensed information in at least the following manners.

The therapeutic or sensory element(s) 130 may be in direct contact with a receiving element. The receiving element may comprise a computing device (e.g., a workstation, a personal computer, a tablet computer, a smartphone, a wearable computer, and the like) or dedicated diagnostic device. The connection may be achieved through the connection of electrical wires to the wound closure device 100, either in a permanent (e.g., "hard-wired") or releasable (via connector) manner. Similarly, heat or cooling by way of a mechanical "plumbing" (e.g., fluid filled tubes) connection, either permanent or releasable, may be employed. For either electrical or mechanical construction, wires or tubes may be routed over, under, or within (embedded, laminated) the closure device 100 using elements such as adhesives, laminates, ties, clips, etc. Arrangement of the connecting elements in a serpentine or other similar pattern may be employed to provide mechanical compliance with the device 100.

The therapeutic or sensory element(s) 130 may be connected with the receiving element wirelessly. A wireless transmitter and/or receiver may be integrated into the closure device 100 to receive and/or send signals with respect to the therapeutic or sensor element(s) 130. This transmitter and/or receiver could, for example, include a battery-operated, low-power Bluetooth or other wireless electrical transmission elements to send/receive to another receiving device such as those described above.

The wound closure device 100 may be a standalone device incorporating activation, sensing, and/or display capabilities for the therapeutic or sensory element(s) 130. The wound closure device 100 may also contain the necessary electrical or mechanical elements to provide therapy or record sensor data. For example, the wound closure device 100 may include a battery-powered data recorder that can be downloaded to another receiving device at planned or random intervals. This connection with the receiving device may also take the form of a self-contained internal feedback loop, where sensor data is monitored and an electrical or mechanical element is activated when sensor data exceeds a pre-set threshold. An example may be a vibration stimulus in the wound closure device 100 notifying the patient when a sensed parameter, such as motion (relative or absolute), temperature or pressure, exceeds a pre-set threshold. Another example may be an optical or magnetic sensor to detect proximity between one or more therapeutic or sensory elements 130.

Sensors.

The following section provides examples of sensors which the therapeutic or sensory element 130 may comprise. Sensors 130 of one type may be integrated into the wound closure device 100, or several different sensors and/or therapeutic elements 130 may be embedded into a single wound closure device 100.

The therapeutic or sensory element(s) 130 may comprise a skin temperature sensing element. The wound closure device 100 may measure temperature using an infrared sensor or using any other way of directly or indirectly measuring the temperature. The temperature sensing element 130 and/or the wound closure device 100 including such an element may be isolated from the surrounding ambient to prevent false reading (e.g., be covered from the outside by an isolating layer or the like). The temperature sensor 130 may record the temperature intermittently or continuously. The temperature sensing wound closure device 100 may be set to send an alarm with an ability to set the temperature required to set off the alarm. Since infection is often associated with hyperemia and increased temperature, the temperature sensing wound closure device 100 may serve as a way for early detection of infection. The alarm could be in many ways—audible, visible LED, vibration, Bluetooth connection to a smartphone or other types of computing devices, etc.

Alternatively or in combination, the therapeutic or sensory element(s) 130 may comprise a mechanical motion sensor. Mechanical motion may be sensed via integrated sensors in the form of strain gauges, electromechanical sensors, electromagnetic sensors, accelerometers, or optical sensors. One or more of the sensors 130 may be used to define changes in position relative to itself and/or other sensors 130 in 3D space, or may simply record binary proximity triggers. The sensor 130 may detect maximum distance or range achieved, or may measure frequency and range of motion over time (e.g., number of times a patient flexes the knee each day during the first three days post-surgery.) Sensor data may be collected via integrated data recording means, or transmitted by wire or wirelessly (e.g., Bluetooth) to an external device such as a dedicated data logger, smartphone application, or other medical device where the data can be presented (e.g., data table, data summary, or graphic form), can be used to trigger an alarm, or can be transmitted to a clinician remotely for patient monitoring without requiring the patient's return to a clinic.

The detection of mechanical motion can alert a practitioner of the range or frequency of mobility of a patient's joint after surgery, for example to monitor compliance with recommended therapeutic regimen after joint surgery or replacement. For example, if a patient is instructed to bend a joint over a certain range and at a certain frequency, this device 100 may alert the practitioner if a patient does not comply with this regimen so that corrective action may be taken. Alternatively or in combination, visual indicators (e.g., via color change) may be utilized to indicate amount or degree of motion. An example would be to detect and indicate maximum range of motion of a joint achieved during successive exercises, to inform the patient when to change or add elements to his/her therapeutic regimen, without requiring the monitoring and input by a clinician. The providing of such indications may reduce the overall cost of therapy by providing a self-guiding program of therapy. Another example may be an audible beep that will be heard when the joint has reached the desired amount of bending (the beeping or alarm could be programmable).

Alternatively or in combination, the therapeutic or sensory element(s) 130 may comprise sensors for determining blood or tissue chemical composition. The sensor(s) 130 may comprise transcutaneous blood composition measurement elements integrated to measure, for example, oxygen, carbon dioxide, glucose, pH, etc. for purposes of assessing wound condition. Transcutaneous oxygen or carbon dioxide measurements may serve as a good indication for tissue vitality, inflammation, infection, etc.

Alternatively or in combination, the therapeutic or sensory element(s) 130 may comprise sensors for detecting mechanical pressure. Mechanical pressure, which can indicate the degree of edema and swelling, can be measured via integrated sensor(s) 130. The degree of swelling may be used to alert a caregiver to administer swelling-reduction therapy (e.g., ice pack) or to automatically trigger or control the temperature of a cold-water circulation system integrated into the device or applied on top of the device.

Alternatively or in combination, the therapeutic or sensory element(s) 130 may comprise one or more therapeutic elements of one or more types that may be integrated into the device 100. Examples of therapeutic types of therapeutic or sensory element(s) 130 are described as follows. While certain types of therapies are described, many other types of therapies which may be delivered through one or more therapeutic or sensory element(s) are also contemplated.

The therapeutic or sensory element(s) 130 may comprise an integrated phototherapeutic delivery element configured to deliver light to the skin. The delivery of light may provide a number of different therapies.

Several different wavelengths of light may stimulate oxygen flow and the body's production of nitric oxide, which in turn may relax muscle fibers and widen blood vessels to increase blood flow to the wound.

Ultraviolet light, especially UV-C, may be delivered to the skin, either continuously or intermittently, to eradicate bacteria and prevent infection. In some embodiments, the device 100 may be battery powered and shine a light in a specific point. In some embodiments, the UV generating device may be connected to an optical fiber that will carry the light and shine it in several locations along the length of the incision. This optical fiber may include a woven or interleaved array of fibers that preferentially leak light as each fiber is bent within the array.

Infrared light may be used to affect mitochondrial enzyme (e.g., cytochrome c oxidase) function in cells that can increase ATP production and improve cellular resistance to ischemia. Infrared light may also stimulate the creation of heat shock proteins which can offer ischemic protection.

Alternatively or in combination, the therapeutic or sensory element(s) 130 deliver mechanical vibration therapy. Mechanical vibration may be integrated into the device 100 and delivered to the skin through the integration of a micro-motor or other vibrating element, and may be used as a therapeutic (e.g., pain reduction) or alerting signal. As a therapy, vibrations at a certain frequency and amplitude may saturate the sensory nerves and reduce pain at the surgical site and/or within surrounding tissues. Ultrasound vibration may be employed for deeper penetration of tissues to aid in local tissue circulation. As an alarm, vibration may be used to alert the patient of an event that requires action, such as the detection of elevated temperature or swelling.

Alternatively or in combination, the therapeutic or sensory element(s) 130 may deliver therapeutic chemicals or drugs. The device 100 may integrate an element by which a chemical agent is delivered to the skin continuously (constant concentration or tapered over time), intermittently, event-driven (such as when the skin exceeds a certain temperature), or upon demand (such as by pressing a button or feature on the device). The chemical agent may be embedded into the device materials, or may be stored in a separate but connected reservoir. Delivery may be passive or active, such as via iontophoretic or electromotive drug administration (EMDA) to deliver a medicine or other chemical through the skin, via transdermal micro needle array, via application to the skin via micro-nozzles (e.g., spray), or high pressure micro bursts of fluid capable of local tissue disruption and agent delivery.

Alternatively or in combination, the therapeutic or sensory element(s) 130 may deliver heat therapy. Small heating elements may be embedded into the device 100 that may be used to provide localized heat to the wound site.

Alternatively or in combination, the therapeutic or sensory element(s) 130 may deliver cooling therapy. The wound site may be cooled through the introduction of cooled air or water to the skin. The cooling element(s) may be integrated into the device 100 in the form of embedded channels to carry the cooling medium at or near the skin where it absorbs heat from the skin (effectively cooling the skin) and is circulated back to a cooling/pump system. Cooling can reduce the sensation of pain and can reduce swelling at the wound site.

Alternatively or in combination, the therapeutic or sensory element(s) 130 may deliver electrical signal. The application of electrical signals, for example weak current, can be used to minimize proliferation of bacteria at the wound site and can be used to promote healing. Higher radiofrequency current could also be employed for local coagulation of blood within tissues of patients prone to bleeding complications (e.g., on Heparin, Warfarin or Plavix).

Alternatively or in combination, the therapeutic or sensory element(s) 130 may ultrasound as a therapy.

Figure 13:
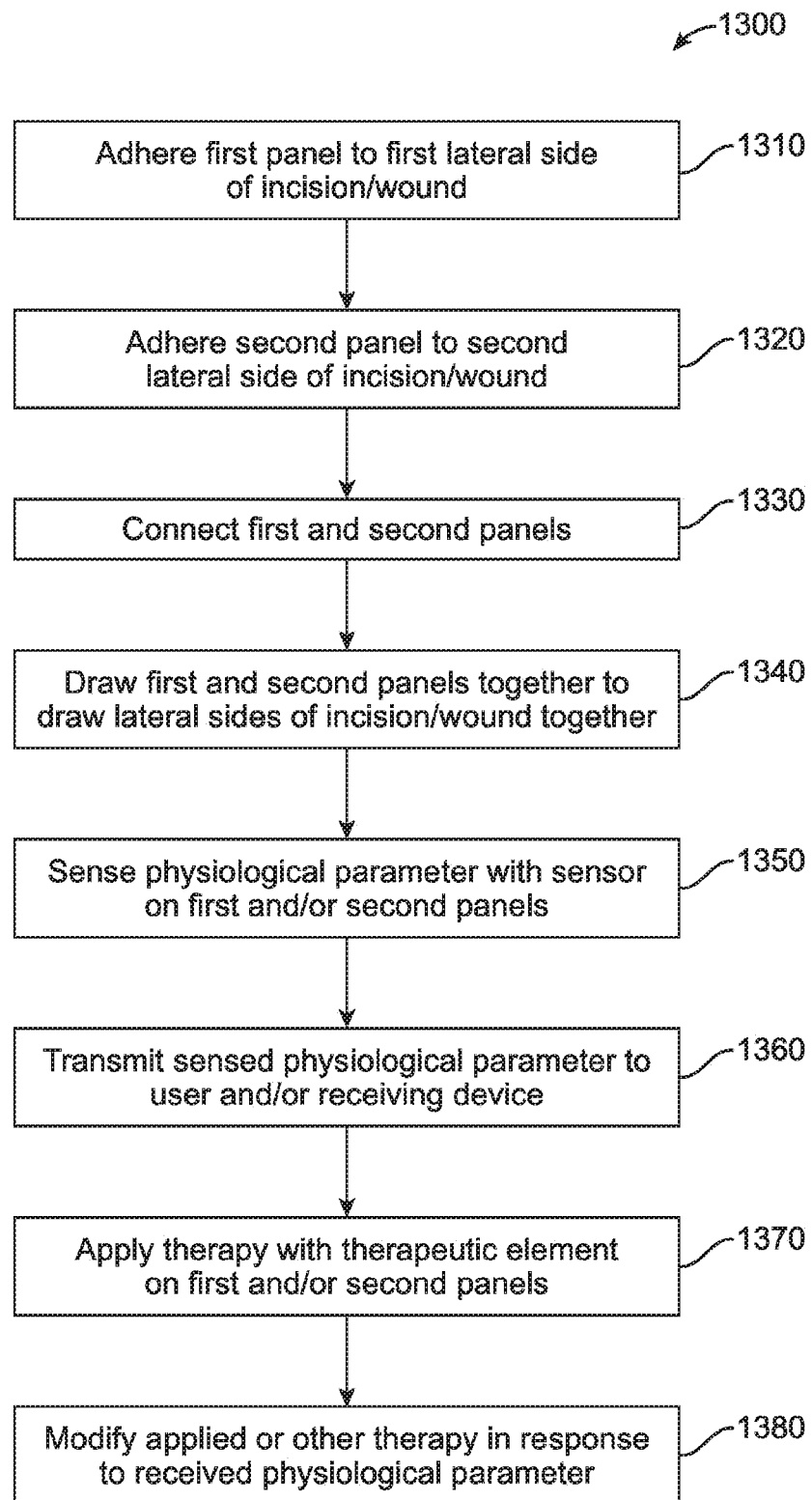
FIG. 13 shows a flow chart of a therapeutic method using a wound closure apparatus with an integrated therapeutic or sensory element, according to many embodiments.

FIG. 13 shows a flow chart of a therapeutic method 1300 using a wound closure apparatus with an integrated therapeutic or sensory element such as device 100 described above. In a step 1310, the first panel 102 of the wound closure apparatus 100 may be adhered to a first lateral side of an incision or wound of a patient. In a step 1320, the second panel 104 of the wound closure apparatus 100 may be adhered to a second lateral side of the incision or wound. In a step 1330, the first and second panels 102, 104 may be connected such as by connecting their top load distribution layers with one another with a plurality of anchored straps and strap brackets. In a step 1340, the first and second panels 102, 104 may be drawn together laterally to draw and hold the lateral sides of the incision or wound together. In a step 1350, the therapeutic or sensory element(s) 130 of the closure device 100 may sense one or more physiological parameters in any of the ways described above. In a step 1360, the therapeutic or sensory element(s) 130 may transmit the sensed physiological parameter(s) to the user and/or a receiving device in any of the ways described above. In a step 1370, the therapeutic or sensory element(s) 130 may apply therapy to the patient in any of the ways described above. In a step 1380, the therapy applied by the therapeutic or sensory element(s) 130 or otherwise applied may be modified in response to the physiological parameter(s) received in any of the ways described above.

Although the above steps show the method 1300 of treating a patient in accordance with many embodiments, a person of ordinary skill in the art will recognize many variations based on the teaching described above. The steps may be completed in a different order. Steps may be added or deleted. Some of the steps may comprise sub-steps. Many of the steps may be repeated as often as beneficial to the treatment.

One or more of the steps of the method 1300 may be performed with circuitry of the device 100 and/or the therapeutic or sensory element(s) 130 as described herein. The circuitry may be programmed to provide one or more of the steps of the method 1300, and the program may comprise program instructions stored on a computer readable memory or programmed steps of the logic circuitry such as a programmable array logic or a field programmable gate array.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the inventions of the present disclosure. It is intended that the following claims define the scope of the invention and that methods and structures within the scope of these claims and their equivalents be covered thereby.

The invention claimed is:

1. A method of treating a wound or incision, the method comprising:
adhering a first panel of a closure apparatus adjacent a first lateral side of the wound or incision;
adhering a second panel of the closure apparatus adjacent a second lateral side of the wound or incision;
drawing the first and second panels laterally together to draw the first lateral side and the second lateral side of the wound or incision together; and
providing a therapy to a patient with a therapeutic element, the therapeutic element comprising a sensory element configured to detect a range of motion of a joint of the patient to monitor said joint after surgery, wherein the first and second panels each include a plurality of layers, the therapeutic element being disposed between two or more of the plurality of layers of one or more of the first or second panels;
wherein the first panel comprises a first bottom adhesive layer, a first medial substrate layer, and a first upper load distribution layer comprising a plurality of load distribution elements, and the second panel comprises a second bottom adhesive layer, a second medial substrate layer, and a second upper load distribution layer a plurality of load distribution elements; and
wherein the drawing the first and second panels laterally together comprises connecting the plurality of load distribution elements of the second panel to the plurality of load distribution elements of the first panel with a plurality of lateral ties.

2. The method of claim 1, further comprising sensing a physiological parameter with said therapeutic element, said therapeutic element disposed on or within one or more of the first or second panels.

3. The method of claim 2, further comprising transmitting the sensed physiological parameter to an external receiving device.

4. The method of claim 3, wherein the external receiving device comprises one or more of a workstation, a personal computer, a laptop computer, a tablet computer, a smartphone, a wearable computer, or a dedicated receiver.

5. The method of claim 2, wherein the physiological parameter comprises one or more of temperature, motion, moisture, pressure, a concentration of a physiological marker, pH, oxygen levels, carbon dioxide levels, and glucose levels.

6. The method of claim 2, wherein the sensory element comprises one or more of a thermometer, a chemical sensor, or a pressure sensor.

7. The method of claim 6, wherein the chemical sensor is configured to measure one or more of blood composition, transcutaneous oxygen, transcutaneous carbon dioxide, glucose levels, and pH.

8. The method of claim 1, wherein the therapy comprises one or more of phototherapy, vibration therapy, ultrasound therapy, drug delivery, heat therapy, cooling therapy, or electrical therapy.

9. The method of claim 1, wherein the sensory element comprises a mechanical motion sensor, and wherein the closure apparatus is configured to send an alert regarding a patient's range or frequency of mobility of said joint.

10. The method of claim 9, wherein a visual indicator is used to indicate an amount of degree of motion of said joint.

11. The method of claim 9, wherein an audible indicator is used to indicate an amount of degree of motion of said joint.

12. The method of claim 1, wherein the therapeutic element is disposed within a pocket.

13. The method of claim 1, further comprising transmitting the detected range of motion of the patient's joint to an external device.

14. The method of claim 13, wherein the external device comprises one or more of a workstation, a personal computer, a laptop computer, a tablet computer, a smartphone, a wearable computer, or a dedicated receiver.

15. The method of claim 1, wherein the sensory element comprises one or more of a strain gauge, an electromechanical sensor, an electromagnetic sensor, an accelerometer, or an optical sensor.

16. The method of claim 1, further comprising a second therapeutic element which comprises one or more of a light source for phototherapy, a mechanical vibration element, an ultrasound device, a drug delivery element, a heating element, a cooling element, an electrifying element, and an ultrasound source.

17. The method of claim 16, wherein the closure apparatus further comprises a removable or attachable portion, and wherein the second therapeutic element is attached to the removable or attachable portion.

18. A method of treating a wound or incision, the method comprising:
adhering a first panel of a closure apparatus adjacent a first lateral side of the wound or incision;
adhering a second panel of the closure apparatus adjacent a second lateral side of the wound or incision;
drawing the first and second panels laterally together to draw the first lateral side and the second lateral side of the wound or incision together; and
providing a therapy to a patient with a therapeutic element, the therapeutic element comprising a motion sensor configured to detect a range of motion of a joint of the patient to monitor said joint after surgery,
wherein the first panel comprises a first upper load distribution layer comprising a plurality of load distribution elements, and the second panel comprises a second upper load distribution layer comprising a plurality of load distribution elements,
wherein the drawing the first and second panels laterally together comprises moving the plurality of load distribution elements of the second panel towards the plurality of load distribution elements of the first panel using a plurality of lateral ties; and
wherein the therapeutic element is attached to the upper load distribution layer of one or more of the first or second panels.

* * * * *